(12) United States Patent
Xue et al.

(10) Patent No.: US 8,494,621 B2
(45) Date of Patent: Jul. 23, 2013

(54) METHOD AND APPARATUS WITH REDUCED ELECTRODE SYSTEM SPECIFIC ECG INTERPRETATION

(75) Inventors: Joel Q. Xue, Germantown, WI (US); Donald E. Brodnick, Cedarburg, WI (US)

(73) Assignee: General Electric Company, Schenectady, NY (US)

( * ) Notice: Subject to any disclaimer, the term of this patent is extended or adjusted under 35 U.S.C. 154(b) by 20 days.

(21) Appl. No.: 13/187,002

(22) Filed: Jul. 20, 2011

(65) Prior Publication Data

US 2011/0275950 A1 Nov. 10, 2011

Related U.S. Application Data

(62) Division of application No. 11/536,716, filed on Sep. 29, 2006, now Pat. No. 8,005,531.

(51) Int. Cl.
*A61B 5/0428* (2006.01)

(52) U.S. Cl.
USPC ........................................................ 600/509

(58) Field of Classification Search
USPC ................. 600/508, 509, 512, 515, 522–523
See application file for complete search history.

(56) References Cited

U.S. PATENT DOCUMENTS

| | | | |
|---|---|---|---|
| 5,792,066 | A | 8/1998 | Kwong |
| 6,282,440 | B1 | 8/2001 | Brodnick et al. |
| 6,507,753 | B1 | 1/2003 | Xue et al. |
| 6,636,761 | B2 | 10/2003 | Brodnick |
| 6,643,539 | B2 | 11/2003 | Meij et al. |
| 7,330,750 | B2 | 2/2008 | Erkkila et al. |
| 7,519,416 | B2 | 4/2009 | Sula et al. |
| 7,702,382 | B2 * | 4/2010 | Xue et al. ...................... 600/509 |
| 2002/0035334 | A1 | 3/2002 | Meij et al. |
| 2002/0045837 | A1 | 4/2002 | Wei et al. |
| 2003/0204384 | A1 * | 10/2003 | Owechko et al. ................. 703/1 |
| 2006/0025695 | A1 | 2/2006 | Wei |
| 2006/0165174 | A1 | 7/2006 | Bernard et al. |
| 2006/0235317 | A1 | 10/2006 | Wei |

FOREIGN PATENT DOCUMENTS

| | | |
|---|---|---|
| JP | 05-000131 A | 1/1993 |
| JP | 10-192251 A | 7/1998 |
| JP | 2001-204701 A | 7/2001 |

(Continued)

OTHER PUBLICATIONS

Atoui et al, "A Neural Network Approach for Patient-Specific 12-Lead ECG Synthesis in Patient Monitoring Environments", Computers in Cardiology, 2004, pp. 161-164.
Kors et al, "Accurate Automatic Detection of Electrode Interchange in the Electrocardiogram", The American Journal of Cardiology, vol. 88, Aug. 15, 2001, pp. 396-399.
Chinese Office Action dated May 26, 2010.

(Continued)

*Primary Examiner* — Carl H Layno
*Assistant Examiner* — Paula J Stice
(74) *Attorney, Agent, or Firm* — Andrus, Sceales, Starke & Sawall, LLP (57) ABSTRACT

A method and apparatus for processing electrocardiographic signals of a patient. The apparatus comprises ten or fewer electrodes connected to a patient at least one of the standard twelve lead ECG electrode positions. The apparatus further comprises a plurality of ECG interpretation algorithms, each of the algorithms specifically tailored for analyzing a twelve lead ECG comprising both measured and derived ECG leads. The method of the present invention comprises determining whether an ECG lead is measured or derived and selecting an ECG interpretation algorithm based upon this determination.

11 Claims, 5 Drawing Sheets

FOREIGN PATENT DOCUMENTS

| | | |
|---|---|---|
| JP | 2002-172096 A | 6/2002 |
| JP | 2005-323821 A | 11/2005 |
| WO | 2004075748 A1 | 9/2004 |

OTHER PUBLICATIONS

"A practical guide to ecg monitoring and recording", ECG Workshop—guide to leads, wires and electrode placement, updated Apr. 1, 2006, http://www.mikecowley.co.uk/leads.htm.

"Ask the Experts: 20 (2) 15-18 Lead ECG Placement", Apr. 2000, vol. 20, No. 2, http://www.aacn.org/accn.practicensf.

US Office Action dated Jan. 27, 2010.

US Office Action dated Jun. 15, 2010.

US Office Action dated Jan. 19, 2011.

JP Notice of Allowance from corresponding JP Application 2007-201968, dated Aug. 7, 2012.

* cited by examiner

METHOD AND APPARATUS WITH REDUCED ELECTRODE SYSTEM SPECIFIC ECG INTERPRETATION

This application is a divisional of U.S. patent application Ser. No. 11/536,716, filed Sep. 29, 2006, now U.S. Pat. No. 8,005,531, issued on Aug. 23, 2011.

FIELD OF THE INVENTION

The present invention relates to a method and apparatus for the enhanced interpretation of an electrocardiogram by specifically tailoring the interpretation algorithm to the source of the electrocardiographic signals used to create the electrocardiogram.

BACKGROUND OF THE INVENTION

A standard twelve lead electrocardiogram (ECG) is obtained using an arrangement of ten electrodes placed at specific locations on the patient's body. It is understood within the present invention that an electrode is a solid electrical conductor placed on the patient's body through which an electric current enters or leaves the patient's body. It is further understood that within the present invention a lead is an electrical slice or view of the patient's heart with respect to the electrocardiographic signal obtained at one or more electrocardiographic electrodes. In a standard twelve lead ECG, four of the ten electrodes are placed on the patient's limbs and the other six electrodes are placed over the patient's heart and across the left side of the patient's chest. Typically, electrocardiographic signals are obtained from each of the ten electrodes and processed to generate the twelve leads of the ECG. The twelve leads are further split into two groups of six ECG leads: the frontal plane leads (I, II, III, aVR, aVL, and aVF) and the horizontal plane leads (V1, V2, V3, V4, V5, V6).

While the standard twelve lead ECG is very useful in obtaining valuable information regarding the patient's heart and cardiac function, it is sometimes undesirable to attach ten electrodes to the patient to obtain the data necessary for a twelve lead ECG. Systems have been developed, such as that disclosed in U.S. Pat. No. 4,850,370, to provide a solution to limit the number of electrodes that must be attached to the patient to obtain all of the desired electrocardiographic information. The '370 patent discloses a novel arrangement of four electrodes on the patient's chest to obtain cardiographic data. However, the system shown in the '370 patent is limited because the electrocardiographic signals produced from this electrode arrangement are inherently different than a standard twelve lead ECG due to the different electrode placements. Much of a cardiologist's or clinician's ability to accurately interpret ECG data is based upon their familiarity with the signals produced at each of the ECG leads. The differences in the electrocardiographic signals produced from an implementation of the '370 patent as compared to a standard twelve lead system requires that the cardiologist or clinician learn an entirely new set of ECG waveforms.

To address these problems, systems such as disclosed in U.S. Pat. No. 6,636,761 to Brodnick have been developed that use some of the ten electrode placements required for a standard twelve lead ECG to monitor some of the twelve leads and to mathematically derive the other unmonitored leads. In an embodiment of the '761 patent, only the four limb electrodes and two precordial (chest) electrodes are utilized to obtain patient information, but in other embodiments more or less of the ten electrode placements may be used.

While the implementation of the system described in the '761 patent provides ECG data to clinicians in a form that they are used to interpreting while at the same time reducing the number of electrodes to be attached to the patient, automated ECG interpretation systems have difficulty interpreting results from systems that include derived ECG leads. While the derived ECG leads are typically accurate in terms of the signal interval and duration, there may be errors in the amplitude of some of the derived ECG leads. The amplitude difference in the derived ECG as compared to the actual lead if monitored can be enough to alter the automated interpretation of the ECG if the interpretation is based heavily upon the amplitude of the derived ECG leads.

A specific example of this potential error is the detection of anterior myocardial infarction (MI), especially acute MI. The automated detection of anterior MI utilizes precordial leads V2, V3 and V4, which in a preferred embodiment of the '761 patent are replaced by the monitoring of leads V1 and V5 coupled with the derivation of V2, V3, and V4. Thus, the automated detection of anterior MI relies upon only derived leads. Therefore, any error in the amplitude measure for the derived leads can alter the automated interpretation of the ECG with respect to the detection of anterior MI. The use of the standard twelve lead ECG interpretation algorithms with the derived ECG leads is estimated to account for a reduction of approximately 10% to 15% in the accuracy of the automated detection of anterior MI.

Therefore, it is desirable in the field of ECG collection and automated ECG interpretation to develop a method and apparatus for the improved automated interpretation of ECG leads that are collected from fewer than ten ECG electrodes.

SUMMARY OF THE INVENTION

The present invention provides a method and apparatus for improved accuracy in the automated interpretation of a twelve lead ECG signal that is collected from fewer than ten ECG electrodes placed on the patient's body. By the present invention, the source of each of the collected electrocardiographic signals is identified as to the locations on the patient's body to which electrodes are placed. Once the electrocardiographic signals from each of the electrodes have been identified, a twelve lead ECG is derived from the collected electrocardiographic signals, using the leads that are measured directly from the measured electrocardiographic signals and mathematically deriving the ECG leads for the leads that are not measured directly. An interpretation algorithm is applied to all of the ECG leads, where the interpretation algorithm is specifically tailored to interpret the specific combination of electrode placements utilized in obtaining the ECG.

In a further embodiment of the present invention, the interpretation algorithms are created based upon the analysis of a plurality of model ECG signals. In a more specific embodiment of the present invention, the model ECG signals are analyzed using an artificial neural network to obtain the interpretation algorithm. In another embodiment of the present invention, the model ECG signals are analyzed using an entropy gain based binary decision tree to develop the interpretation algorithms.

In a still further embodiment of the present invention, a standard ECG interpretation algorithm is used as the default interpretation algorithm such that if the source electrode signals for the derived ECG are unknown, the system of the present invention applies the standard ECG interpretation algorithm to the derived ECG.

In a still further embodiment of the present invention, the present invention comprises the detection of more than twelve ECG leads utilizing ten or fewer electrodes connected to the patient, some of which are at locations embodied within the standard ten electrode, twelve lead ECG positioning.

DETAILED DESCRIPTION

Figure 1:
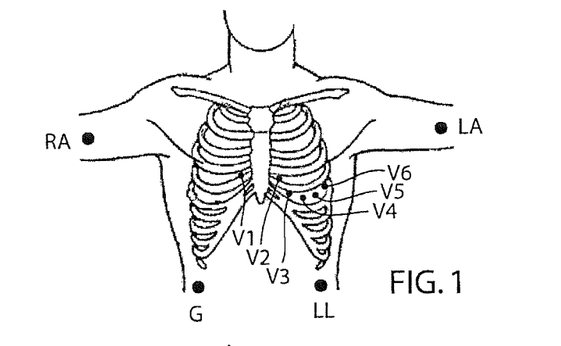
FIG. 1 depicts the placement of the ten electrodes on the patient in a standard twelve lead ECG configuration.

A standard twelve lead ECG is normally acquired with ten electrodes placed at specific locations on the patient's body. FIG. 1 depicts the proper placement of these ten electrodes. Four of the electrodes are placed at the limbs of the patient at or near the patient's wrists or ankles. These four electrodes are indicated as the left arm (LA), the right arm (RA), the left leg (LL), and the right leg (G). The right leg is typically connected to ground in a right leg driven ECG system. By connecting the right leg to ground, the right leg driven system provides increased quality of the electrocardiographic signals obtained at the other electrodes compensating for a reduced common mode rejection ratio for the amplifiers associated with each of the other electrodes. FIG. 1 also depicts the placement of the six chest or precordial electrodes forming a generalized horizontal plane through the patient's heart. It is well known in the art that each of these electrodes is connected via a wire or cable to a signal processing unit where the electrocardiographic signals from each of these electrodes are translated into each of the twelve ECG leads.

Figure 4:
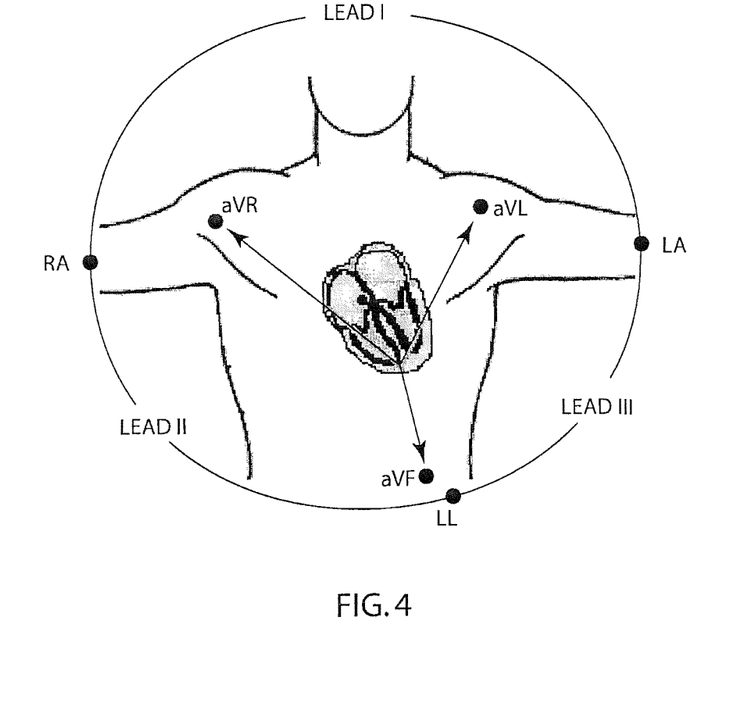
FIG. 4 depicts the six frontal leads of a standard twelve lead ECG.

The twelve ECG leads are further divided into two groups of leads, the frontal leads and the horizontal leads. FIG. 4 depicts the frontal leads of the standard twelve lead ECG. The frontal leads are obtained by comparing the ECG signals obtained at each of the limb electrodes: RA, LA, and LL. Lead I is the potential between RA and LA electrodes. Lead II is the difference in potential between the RA and LL electrodes. Lead III is the difference between the LA and the LL electrodes. The other three frontal leads are referred to as the augmented leads and represent the potential difference between one limb electrode and the average of the other two limb electrodes. For example, the lead aVR is the potential difference between the RA electrode and the reference comprising the average of the potentials of the LA and LL electrodes.

Figure 5:
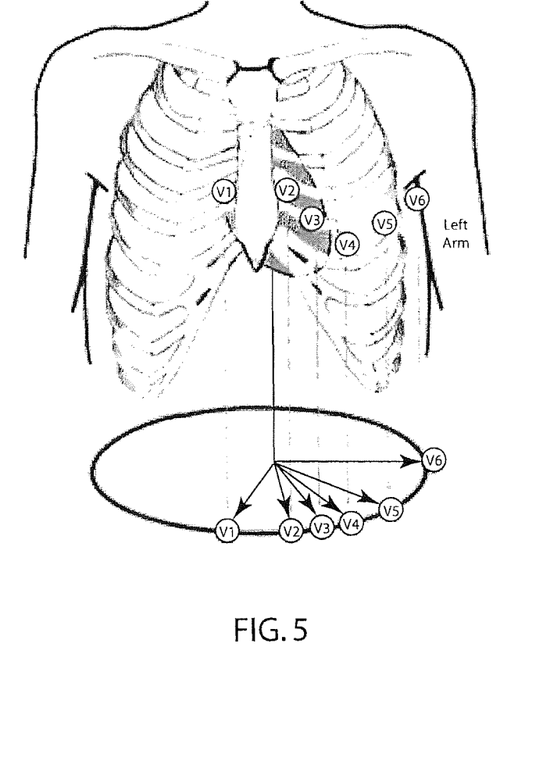
FIG. 5 depicts the six horizontal leads of a standard twelve lead ECG.

FIG. 5 depicts the six leads in the horizontal plane. By reference to FIG. 5, each of the horizontal leads V1-V6 are the difference in potential between one of the precordial electrodes and a central reference point. This central reference point is known as Wilson's Central Terminal. Wilson's Central Terminal is equal to the average potential between the three limb electrodes (RA, LA, LL).

Figure 2:
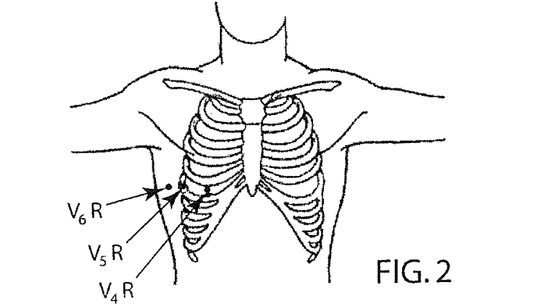
FIG. 2 depicts the electrode placements for obtaining the right precordial ECG leads.
Figure 3:
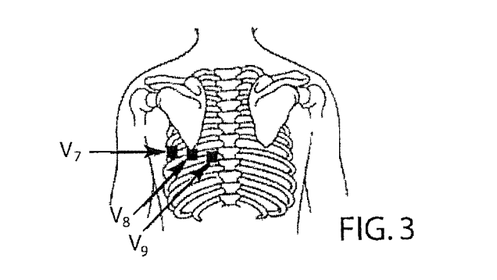
FIG. 3 depicts the electrode placement for obtaining the left side posterior leads.

Beyond the standard twelve lead ECG leads, additional leads may be utilized by a clinician for further precision in analyzing cardiac function. The placement of the additional necessary precordial electrodes to obtain these leads are depicted in FIGS. 2 and 3. FIG. 2 depicts the placement of the right precordial electrodes. These electrodes denoted as V4$r$, V5$r$ and V6$r$ are placed at the mirrored location as the corresponding V4, V5 and V6 precordial electrodes and are used by a clinician to better observe the function of the right side of the heart. Typically, these lead electrodes are placed at specific locations on the patient's body. The V4$r$ electrode is placed at the right midclavicular line, fifth intercostal space. The V5$r$ electrode is placed at the right anterior axillary line, fifth intercostal space. The V6$r$ electrode is placed at the right midaxillary line, fifth intercostal space.

FIG. 3 depicts the placement of the three left side posterior electrodes (V7, V8, and V9). The left side posterior electrodes continue the electrode sequence around the left side of the patient from the standard precordial electrode (V1-V6) placements. The V7 electrode is placed on the left posterior axillary line, fifth intercostal space. The V8 electrode is placed at the left midscapular line, fifth intercostal space. The V9 electrode is placed at the left paraspinal line, fifth intercostal space.

The leads associated with the additional electrodes depicted in FIGS. 2 and 3 are similar to the standard precordial leads depicted in FIG. 5 on approximately the same horizontal plane as the other precordial leads. Therefore, there is a possibility of obtaining up to eighteen ECG leads to facilitate a clinician's interpretation of the patient's cardiac function. However, most current ECG monitoring equipment is limited to only the standard ten ECG electrodes. Therefore, if a clinician desires to obtain additional measurements of patient precordial leads, the clinician must disconnect one of the standard precordial electrodes and reconnect it at one of the alternative locations.

Figure 6:
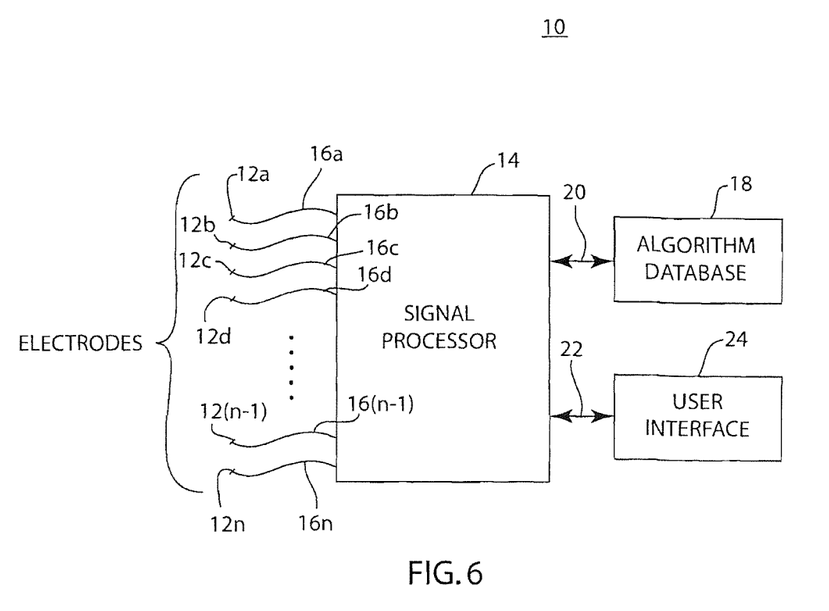
FIG. 6 depicts a schematic diagram of an embodiment of the present invention.

FIG. 6 depicts a schematic diagram of an embodiment of the medical device 10 of the present invention. The medical device 10 comprises a plurality of electrodes 12 $a$-$n$. It is understood that the electrodes 12 as utilized within the present invention may be any construction of electrode disposed for collecting an electrical signal from the body of a patient. Without limiting the scope of the present invention, the electrode may comprise a metal substrate or thin film of conductive material. The electrode may further comprise a conductive paste or gel. Furthermore, the electrode may be disposable or reusable after sterilization.

The electrodes 12 $a$-$n$ are connected to a signal processor 14 by lead wires 16 $a$-$n$. In accordance with the present invention and without imputing limitation, it is understood that the signal processor 14 may comprise any form of controller, microcontroller, or microprocessor known in the art. Furthermore, the signal processor 14 may comprise a CPU in a desktop computer, laptop computer, or special purpose instrument such as ECG cart or bedside patient monitor or defibrillator. The signal processor 14 has electrical communication capability with an algorithm database 18 via a line 20. It is understood that line 20 may be any standard means of transferring an electric data signal and need not be a physical wire, but may also include wireless communications. Algorithm database 18 need not be physically proximal to the signal processor 14 as the algorithm database 18 may be a centralized data server and may be connected to the signal processor 14 via an internet, intranet, or wireless connection. The signal processor 14 is also in electrical communication with a user interface 24 via line 22. It is further understood that within an embodiment of the present invention, the user interface 24 may comprise a display, a graphical printout, or further signal processing and digital data recordation.

As described in U.S. Pat. No. 6,636,761 to Brodnick, which is herein incorporated by reference, it is unnecessary to obtain ECG signals from each of the ten ECG electrode locations for a standard twelve lead ECG. The reduction in the number of leads is possible due to redundancy in the cardiac information present in each of the standard ECG leads. Therefore, a reduced electrode set comprising fewer than ten electrocardiographic electrodes may be used to directly obtain some of the ECG leads, while the information from the other ECG leads may be derived from the electrocardiographic signals obtained from the attached electrodes.

In an embodiment of such a derived twelve lead ECG system, electrodes 12 *a-d* are connected to the four patient limbs at electrode locations RA, LA, LL, and G while electrode 12 (*n*-1) is connected to electrode location V1 and electrode 12*n* is connected to electrode location V5. By techniques known in the art, the averaging and analysis of many precordial electrocardiographic signals can be used to derive an algorithm to determine the other four precordial electrodes (V2, V3, V4, and V6) using the ECG signal collected from electrodes 12*a*-12*n*.

Typically, an ECG analysis program usually includes two main portions, ECG lead measurement followed by interpretation of the measurements. While the algorithms described above used for deriving additional precordial ECG leads produce an accurate representation of the derived ECG leads in terms of ECG morphological feature duration, the ECG lead derivation algorithms as taught in the '761 patent are limited in the derivation of the ECG lead signal amplitudes. While this is of no effect to many standard ECG interpretation algorithms, some standard ECG interpretation algorithms that are heavily reliant upon the amplitude of the leads that have been derived may experience errors in ECG lead interpretation. Therefore, in embodiments of the present invention, ECG lead interpretation algorithms are developed that compensate for any difference in the amplitude of the derived ECG lead signals. This may be accomplished by creating a plurality of ECG interpretation algorithms that are specifically tailored to interpret the ECG derived from a specific combination of ECG electrodes.

Therefore, within the present invention, an ECG lead interpretation algorithm database 18 comprises a plurality of ECG interpretation algorithms. Each algorithm is specifically tailored to interpret a twelve lead ECG comprising a different combination of measured leads and derived leads in the twelve lead ECG.

The ECG lead interpretation algorithms may be developed in a variety of ways. In an embodiment of the present invention, the algorithms are developed by analysis of a plurality of sample twelve lead ECG signals. By the compilation and analysis of many sample ECG signals, an algorithm may be developed that produces an accurate diagnosis of a cardiac condition based upon the morphologies of the twelve leads of the ECG. By specifically tailoring an interpretation algorithm for each combination of measured and derived ECG leads, the errors associated with applying a standard ECG lead interpretation algorithm to an ECG signal comprising measured and derived ECG leads may be avoided.

In an embodiment of the present invention, the specifically tailored interpretation algorithms are derived using a nonlinear regression model based upon an artificial neural network (ANN). The artificial neural network works as a black box that can handle a large amount of complex data as an input and provides as an output an algorithm that most closely represents the conditions associated with the inputted ECG signals. The advantage of this embodiment of the present invention is that the ANN has greater capacity for handling complex ECG data such that it is easier to analyze a larger number of sample ECG lead signals in creating the interpretation algorithm. However, the drawback to the artificial neural network embodiment is that the artificial neural network operates as a black box and, as such, the output is provided without any insight or detail of how the artificial neural network derived the interpretation algorithm.

In a further embodiment of the present invention, a rule induction model based upon a binary decision tree using entropy gain is used to develop the interpretation algorithms used in the present invention. In the binary decision tree embodiment of the present invention, a series of binary questions or decisions are created such that when an ECG signal is entered into the binary decision tree, the system asks a binary question and decides which of the binary categories the ECG signal falls into based upon the entropy gain of a given binary category. The analysis of one binary question leads in a tree formation to another binary question and so on until the ECG signal has been interpreted out to the ends of a branch and thereby specifically identified. The advantage of this system for developing an interpretation algorithm is that a detailed analysis of each ECG signal may be reviewed to provide further data for interpreting the ECG signal. However, the disadvantage of this embodiment is that it is time consuming to develop all of the binary questions and the binary decision tree to produce an effective algorithm based upon this system. Furthermore, analysis of ECG signals using this system is more time consuming and therefore fewer ECG signals may be incorporated into deriving the interpretation algorithm.

In an embodiment of the present invention, a combination of both of the artificial neural network and the binary decision tree interpretation systems are used to provide an interpretation algorithm that comprises both the transparency into how the algorithm was derived, and also the validity of using a large number of ECG sample signals in deriving the interpretation algorithm.

Figure 7:
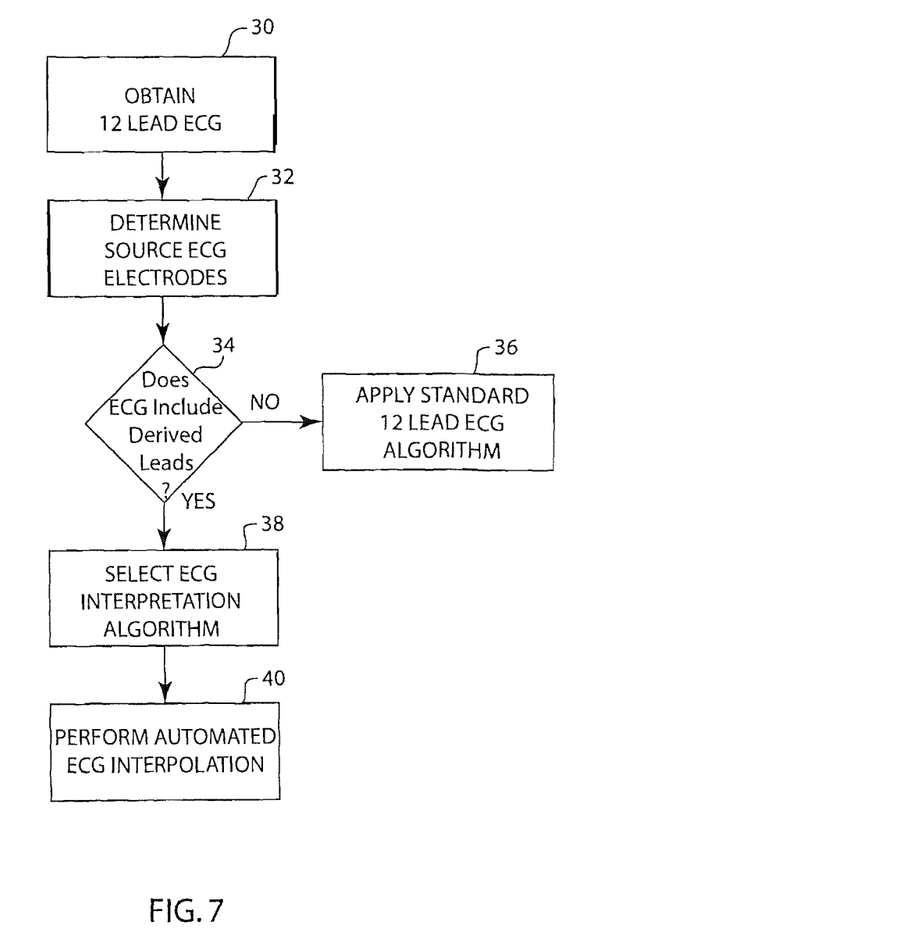
FIG. 7 is a flow chart depicting an embodiment of the method of the present invention.

FIG. 7 is a flow chart depicting the steps of an embodiment of the method of the present invention. First, ECG signals are obtained in step 30. These ECG signals may be obtained via a plurality of electrodes attached to the body of the patient at specific locations such that the electrodes are attached to locations that comprise the standard ten electrode locations for a standard twelve lead ECG. It is understood that the step 30 of obtaining the twelve lead ECG may comprise deriving one or more of the ECG leads from one or more measured electrocardiographic signals.

Next, in step 32, the locations of the electrodes, from which electrocardiographic signals are obtained, are determined. In the determination of the electrode locations of step 32, the electrode positions on the patient's body are identified. The determination in step 32 may be accomplished in a variety of ways, such as an included embedded signal within the received ECG signal that identifies the location to which the electrode is attached. Alternatively, the clinician may define and enter in the locations to which the electrodes are attached. In a further embodiment, the determination of the ECG electrode locations is performed using lead detection and analysis to identify the locations on the patient to which the electrodes are attached. Such a method is described in U.S. Pat. No. 6,282,440 to Brodnick, which is herein incorporated by reference. It is understood that many other ways of identifying electrode location are possible and within the scope of the present invention.

Next, in step 34, the twelve lead ECG is analyzed to determine whether it comprises any derived ECG leads. If no ECG leads in the twelve lead ECG are derived, or if it is unknown whether any of the leads of the twelve lead ECG are derived, then the standard twelve lead ECG interpretation algorithm is applied in step 36. This standard twelve lead ECG interpretation algorithm may comprise any such interpretation algorithm that is commonly used to interpret a standard twelve lead ECG.

If it is determined that one or more of the leads in the twelve lead ECG have been derived, then an appropriate ECG interpretation algorithm must be selected in step 38. The selection of the ECG interpretation algorithm is made with reference to the determination of the source ECG electrode locations in step 32. The combination of the locations on the patient to which electrodes are attached in obtaining the twelve lead ECG will determine the appropriate ECG interpretation algorithm to be selected in step 38. The selection may be made from a plurality of interpretation algorithms specifically tailored to interpret an ECG comprising a specific combination of measured and derived ECG leads.

The selection of the appropriate specifically tailored interpretation algorithm may comprise an analysis of which ECG leads are measured and which ECG leads are derived. This is dependent upon the number and location of the electrodes placed on the patient. In an embodiment of the present invention, the specifically tailored interpretation algorithms are each matched to a combination of measured and derived leads. After the determination in step 32, the measured ECG leads and the derived ECG leads are known, therefore the proper specifically tailored interpretation algorithm may be selected. By means of a non-limiting example, a first exemplary interpretation algorithm may be matched to the combination of ECG leads where leads I, II, III, V1, and V5 are measured and leads V2, V3, V4, and V6 are derived; while a second exemplary interpretation algorithm may be matched to the combination of ECG leads where leads I, II, III, V1, V3, and V5 are measured and leads V2, V4, and V6 are derived. The second exemplary interpretation algorithm would differ from the first exemplary algorithm in that the second exemplary interpretation algorithm would take the additional measured lead (V3) data into account in the interpretation.

Once the proper ECG interpretation algorithm has been selected in step 38, the automated ECG interpretation may be performed in step 40 according to the specifically tailored ECG interpretation algorithm selected in step 38. By this method of the present invention, the appropriate specifically tailored ECG interpretation algorithm is applied to the twelve lead ECG comprising derived ECG leads. By interpreting the ECG lead with a specifically tailored interpretation algorithm, automated interpretation problems associated with the derived ECG leads are limited as these specifically tailored interpretation algorithms have been derived in light of known derivation errors and therefore the derived leads are interpreted as such, eliminating the error in the interpretation.

In an embodiment of the invention, one specifically tailored interpretation algorithms may comprise a substantial amount of the same interpretation algorithms as another interpretation algorithm. It is understood that in so much as two interpretation algorithms are matched to a similar combination of ECG leads, the interpretation algorithms will be the same. By means of a non-limiting example, all of the interpretation algorithms for interpreting a combination of electrocardiographic signals from the RA, LA, LL, G electrodes and one or move V electrodes will comprise the same interpretation algorithms for at least the I, II, III, aVR, aVL, and aVF leads, since all of the frontal plane electrodes are present, while the interpretation algorithms for the V leads may differ due to the different measured and derived V leads.

In an alternative embodiment of the present invention, an ECG monitoring system comprising ten electrodes is utilized to obtain greater than twelve leads of ECG data. In an embodiment of the present invention, four of the electrodes are attached to the standard patient limbs and one electrode is attached at the V1 position and another electrode is attached at the V5 position. The remaining four electrodes are attached to one or more of the right precordial patient electrode locations or the left side posterior electrode locations. Thus, in operation of an embodiment of the present invention, the four standard patient limb electrodes and the two patient precordial electrodes (V1 and V5) are used to measure and derive the twelve lead ECG, while the remaining four electrodes are used to measure four additional right precordial and/or posterior ECG leads. Thus in this embodiment, the use of ten electrodes produces the measurement of up to sixteen ECG leads In a still further embodiment of the present invention, the electrodes attached to the patient at the right precordial or the left posterior electrode locations are used to derive additional right precordial or left posterior electrode leads, such that up to eighteen leads of ECG data may be obtained at the same time, from electrocardiographic signals obtained from ten or fewer electrodes. Although this embodiment derives a greater number of ECG leads, the interpretation of the leads may be in accordance with the present invention. The inclusion of more than twelve leads of ECG data into the interpretation algorithms serves to further improve the accuracy of the diagnosis of patient condition based upon the detection of ECG morphological features. In an aspect of this embodiment, interpretation algorithms may be derived to include improved interpretation of greater than twelve ECG leads including additional derived right precordial and anterior precordial leads.

Embodiments of the present invention may be implemented as a software update to an existing ECG device that is already configured to obtain electrocardiographic data from a conventional ten electrode lead set. Alternatively, the software to carry out an embodiment of the present invention may be programmed into a new device or a hospital ECG analysis computer.

The present invention provides advantages over the prior art ECG collection and interpretation systems such that errors associated with the interpretation of derived ECG signal leads are reduced and overall accuracy of automated ECG interpretation is facilitated. Another advantage of the present invention is the increased functionality obtained from a standard ECG collection and interpretation unit comprising ten standard ECG collection electrodes. The increased functionality of the collection of additional leads of ECG information without adding additional ECG electrodes provides a clinician with a greater picture of the patient's cardiac function, thus improving diagnosis and monitoring of the patient's cardiac health. A further advantage of the present invention is that in an embodiment, the functionality of a standard ten electrode ECG device may be improved to operate the ECG collection and interpretation features of the present invention by updating the software of the ten electrode ECG device. This enables a healthcare institution to provide greater patient monitoring functionality while limiting the need for purchasing a new costly medical device.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being within the scope of the following claims, particularly pointing out and distinctly claiming the subject matter regarded as the invention.

What is claimed is:

1. A medical device for receiving electrocardiographic signals from a patient and analyzing the signals to produce a diagnosis of patient condition, the medical device comprising:
    a plurality of ten or fewer electrodes for attachment to the patient in at least one of ten standard ten-electrode positions;
    an interpretation algorithm database comprising a plurality of interpretation algorithms, each algorithm in the plurality designed to produce the diagnosis of patient condition when applied to an electrocardiogram and each algorithm in the plurality corresponding to a combination of respective positions of the plurality of ten or fewer electrodes each in one of the standard ten-electrode positions; and
    a signal processor connected to the plurality of electrodes, the signal processor disposed for receiving electrocardiographic signals from each of the plurality of electrodes and generating a twelve lead electrocardiogram from the electrocardiographic signals;
    wherein the signal processor identifies the combination of respective positions of the plurality of electrodes, selects the corresponding algorithm from the interpretation algorithm database based upon the positions of the plurality of electrodes and uses the selected algorithm to analyze the twelve lead electrocardiogram.

2. The medical device of claim 1, further comprising a standard interpretation algorithm designed to produce the diagnosis of patient condition when applied to an electrocardiogram where each of the leads in the twelve lead electrocardiogram is a measured electrocardiographic signal obtained from the electrodes connected to the patient, wherein the signal processor further selects the standard interpretation algorithm if the processor is unable to identify the combination of respective positions of the plurality of electrodes.

3. The medical device of claim 1, wherein the interpretation algorithms comprise the analysis of a plurality of electrocardiographic signals.

4. The medical device of claim 3, wherein the plurality of electrocardiographic signals comprises electrocardiographic signals selected to be representative of an electrocardiographic morphology.

5. The medical device of claim 4, wherein the analysis of the plurality of electrocardiographic signals is performed using an artificial neural network.

6. The medical device of claim 4, wherein the analysis of the plurality of electrocardiographic signals is performed using a binary decision tree.

7. The medical device of claim 6, wherein the binary decision tree uses entropy gain.

8. A method of producing a diagnosis of patient condition, the method comprising:
    obtaining electrocardiographic signals from a plurality of ten or fewer electrodes connected to the patient at locations on the patient corresponding to the ten standard electrode placements for obtaining a twelve lead electrocardiogram;
    identifying, with a signal processor, a location on the patient to which each of the electrodes is connected based upon analysis by the signal processor of the obtained electrocardiographic signals;
    deriving, with the signal processor, a twelve lead electrocardiogram from the obtained electrocardiographic signals;
    selecting an algorithm from an interpretation algorithm database with the signal processor based on the identified locations on the patient to which each of the electrodes is connected wherein the interpretation algorithm database comprises a plurality of interpretation algorithms, each algorithm in the plurality designed to produce the diagnosis of patient condition when applied to an electrocardiogram and each algorithm in the plurality corresponding to a combination of placements of the plurality of ten or fewer electrodes in one of the standard ten-electrode positions;
    analyzing the derived twelve lead electrocardiogram by applying the selected algorithm to the derived twelve lead electrocardiogram with the signal processor; and
    determining, with the signal processor, the diagnosis of patient condition from the analysis of the derived twelve lead electrocardiogram&

9. The method of claim 8, further comprising the step of receiving an embedded signal indicative of electrode placement, wherein the determination of the locations on the patient to which the electrodes are attached is based upon the embedded signal.

10. The method of claim 8, further comprising measuring the electrocardiogram leads from each of the electrodes, wherein the twelve lead electrocardiogram is derived using the measured electrocardiogram leads.

11. The method of claim 10, wherein the twelve lead electrocardiogram is derived by mathematically deriving any leads associated with any of the standard ten electrode locations to which an electrode is not attached.

* * * * *